United States Patent [19]
Maciak et al.

[11] Patent Number: 5,264,341
[45] Date of Patent: Nov. 23, 1993

[54] SELECTIVE CLONING FOR HIGH MONOCLONAL ANTIBODY SECRETING HYBRIDOMAS

[75] Inventors: Ronald S. Maciak; Philip Marder, both of Indianapolis, Ind.

[73] Assignee: Eli Lilly and Company, Indianapolis, Ind.

[21] Appl. No.: 400,643

[22] Filed: Aug. 30, 1989

[51] Int. Cl.$^5$ .................. C12N 15/02; G01N 33/577
[52] U.S. Cl. ............................. 435/7.21; 435/7.24; 435/30; 435/172.2; 435/240.27; 435/948; 436/548
[58] Field of Search ............ 435/7.1, 7.2, 7.21, 435/7.22, 7.24, 172.2, 240.27, 968, 30, 243, 948; 436/63, 64, 548

[56] References Cited

U.S. PATENT DOCUMENTS 4,474,893 10/1984 Reading ........................ 436/547
4,894,348 1/1990 Ronald et al. .................. 436/546

OTHER PUBLICATIONS

L. E. Hood et al, *Immunology*, Second Edition, The Benjamin/Cummings Publishing Company, Inc., Menlo Park, CA, 1984, pp. 17-19.
G. Galfrè et al, *Meth. Enzymol.*, 73, 3-46, 1981.
P. J. Leibson et al. Clonal Evolution of Myeloma Cells Leads to Quantitative Changes in Immunoglobulin Secretion and Surface Antigen Expression, *Proc. Natl. Acad. Sci.*, vol. 76, No. 6, pp. 2937-2941, (Jun. 1979).
Andreas Radbruch et al., Isolation of Variants of Mouse Myeloma X63 that Express Changed Immunoglobulin Class, *Proc. Natl. Acad. Sci.*, vol. 77, No. 5, pp. 2909-2913, (May 1980).
Larry W. Arnold et al., Ig Isotype Switching in B Lymphocytes, *The Journal of Immunology*, vol. 140, No. 12, pp. 4355-4363, (Jun. 1988).
Francois Martel et al., Characterization of Higher Avidity Monoclonal Antibodies Produced by Murine B-Cell Hybridoma Variants Selected for Increased Antigen Binding of Membrane Ig$^1$, *The Journal of Immunology*, vol. 141, No. 5, pp. 1624-1629, (Sep. 1988).
Eliane Meilhoc et al., Application of Flow Cytometric Measurement of Surface IgG in Kinetic Analysis of Monoclonal Antibody Synthesis and Secretion by Murine Hybridoma Cells, *Journal of Immunological Methods*, vol. 121, pp. 167-174, (1989).

*Primary Examiner*—David Saunders
*Attorney, Agent, or Firm*—Ronald S. Maciak; Leroy Whitaker

[57] ABSTRACT

The invention is a method for selectively isolating cells which secrete higher levels of monoclonal antibody than did the parental culture from which they were derived. The method is based on the membrane characteristics of the cell and requires the use of a cell sorter. At present, the invention's best mode utilizes fluorescent probes in conjunction with a fluorescence activated cell sorter. The method is based on the correlation of a high level of cell surface immunoglobulin with high monoclonal antibody secretion rates. The invention provides a predictable and rapid process for selecting high monoclonal antibody producing cells.

24 Claims, No Drawings

SELECTIVE CLONING FOR HIGH MONOCLONAL ANTIBODY SECRETING HYBRIDOMAS

TECHNICAL FIELD OF INVENTION

This invention belongs to the field of hybridoma technology and provides a predictable and rapid process for selecting and cloning cells which secrete higher than normal levels of monoclonal antibody (MAb). The process is based on the selection of those cells which present a higher than average density of immunoglobulin on their cell surfaces.

BACKGROUND

Monoclonal antibodies have become major constituents of the burgeoning field of biotechnology related products. It has become apparent that for the development and general distribution of MAb diagnostic and therapeutic products, large scale production techniques will be necessary.

Although MAbs can be produced in vivo by collection of ascitic fluid, in vitro mass cell culture is in many ways preferable (Samoilovich et al., 1987, Hybridoma technology: new developments of practical interest. *J. Immunol. Methods* 101, 153). Due to the significant production expenses incurred in these large scale cultures, obtaining maximal yields of reactive MAb is indeed important (Velez et al., 1986, Kinetics of monoclonal antibody production in low serum growth medium. *J. Immunol. Methods* 86, 45); (Reuveny et al., 1986, Comparison of cell propagation methods for their effect on monoclonal antibody yield in fermentors. *J. Immunol. Methods* 86, 53). To date, most reports in this area describe methods for improving MAb yields by optimizing media formulations and by controlling environmental culture conditions (Samoilovich et al., supra). Lacking, however, are discussions of the selection and maintenance of initial variant hybridoma starter cultures capable of secreting increased MAb concentrations.

The method for producing monoclonal antibodies was first described by Kohler and Milstein in 1975. Since that time, many variations and improvements have been made on their process (for a general review, see *Methods in Enzymology*, 121, 1986). This invention is not concerned with the process of constructing new hybridomas but rather focuses on the cloning and re-selection of existing hybridoma cell lines.

Hybridoma cells result from the fusion of tetraploid myeloma cells with diploid, antigen stimulated lymphocytes. The myeloma cell partner confers the ability to grow indefinitely in culture while the genetic information which codes for antibody specificity and type emanates from the lymphocyte. The resultant hybridoma cell is capable of growing indefinitely and secreting a uniformly consistent and homogeneous MAb of known specificity. Due to its polyploid nature, the resultant hybridoma is also genetically unstable. Genetic instability of hybridomas is a well documented fact which can, over time, lead to profound phenotypic changes. Quite frequently, hybridoma cultures will decrease the rate at which they secrete MAb and correspondingly increase their growth rate. The combined result of those changes causes the culture gradually to lose its capacity to produce and secrete MAb while consuming ever increasing amounts of substrate which results only in greater cell mass rather than MAb. Isotype switching is another phenotypic change which can occur as a hybridoma cell line is left in continuous culture. Isotype switching occurs when small sub-populations of cells within a culture change over to a different protein backbone (isotype) while maintaining the identical antigen specificity. The most detrimental phenotypic change which a hybridoma culture may undergo is to lose its capacity for growth. This phenomenon is fairly common and occurs quite rapidly when cells expel or fail to replicate a chromosome which encodes a structural protein or enzyme essential for growth. In order to avoid or circumvent some of the undesired characteristics mentioned, frequent and continual re-selection or cloning of hybridoma cultures is essential so that a genetically stable, homogeneous cell line can be maintained.

Hybridoma cultures are cloned using any one of three basic techniques, cloning by limiting dilution, cloning over soft agarose, or cloning by fluorescence activated cell sorting. Cloning by limiting dilution is accomplished by randomly selecting a small group of cells which is then diluted into growth medium at a very low concentration. Small aliquots of the cell suspension, which theoretically contain one or less cells, are then placed into individual growth wells where they may grow into new cultures.

Cloning over soft agarose is accomplished by making very dilute cell suspensions in warmed growth medium containing a suitable amount of agarose. A volume of the cell suspension, which theoretically contains ten to one hundred cells, is plated into a petri dish where it is allowed to cool and solidify. As individual cells grow and divide, colonies of cells result which are held in place by the semi-solid medium. This technique is directly analogous with pour plates in bacteriology.

Lastly, fluorescence activated cell sorting can facilitate the cloning of a hybridoma culture. In this case, laser light is directed at individual cells as they flow through the instrument in a stream of single cells. A light scatter pattern is generated when the dense nuclear material of the cell interferes with the path of the laser beam. Thus, cells can be selected at random based on their ability to scatter laser light. After a cell has been identified, it is deflected away from the stream of cells and is directed into a growth well by means of an automated cell cloning device. The flow method affords a distinct advantage over those previously described in that the fluorescence activated cell sorter is capable of depositing one and only one cell into a particular growth well. The other methods rely on theoretical calculations which statistically make the chances of one cell per well or one cell per unit area likely rather than assured.

All three of the aforementioned techniques rely on the random selection of cells. The successful isolation of a clone with desirable MAb secretion characteristics is no more predictable than the laws of random probability will allow.

SUMMARY OF THE INVENTION

The invention comprises a method of selectively isolating a population of cells which secrete monoclonal antibody of known specificity at a level higher than the parent culture from which they were derived and which have immunoglobulin associated with, and presented on the outer surface of, the plasma membrane, wherein cells of the parent culture are contacted with a probe which preferentially binds to the immunoglobulin and those cells having high probe intensity are isolated by means of a cell sorter. The invention further comprises a method of individually depositing the selected cells into separate growth wells by means of a cell sorter outfitted with an automated cloning accessory. Lastly, the invention also comprises a method of rescuing the monoclonal antibody secreting capacity of an essentially non-secreting hybridoma culture.

DETAILED DESCRIPTION OF THE INVENTION

While the following detailed discussion of the invention focuses on fluorescent probes and fluorescence activated cell sorters, other methods of detection of immunoglobulin on the cell surface are entirely usable. The following descriptions that employ fluorescent probes and fluorescence activated cell sorters are merely used to illustrate the present invention. Fluorescence detection is preferred, however.

A hybridoma cell is a eukaryotic cell which is formed by the fusion of one or more myeloma cells with one or more lymphocytes. Numerous different types of myeloma cells are commercially available through the American Type Culture Collection (Rockville, Maryland) and Ventrex Laboratories, Inc. (Portland, Maine). Lymphocytes can be obtained from a variety of organ sites located within an immunized donor. Most typically, the sites are the spleen, the lymph nodes and the blood. Examples of established hybridoma cell lines that are stored and catalogued by the American Type Culture Collection (ATCC) on which this invention could be utilized follow:

| Antigenic determinant | Type | Designation | ATCC No. |
|---|---|---|---|
| Acetylcholinesterase, human | $IgG_1$ | AE-2 | HB73 |
| Actin, prokaryotic | $IgG_1$ | ACT I | HB 80 |
| Bacterial adhesins (K99 pili) | IgG | 2BD4E4 K99 | HB 8178 |
| Carcinoembryonic antigen (CEA), high mw | IgM | 1116NS-3d | CRL 8019 |
| Choriocarcinomas | $IgG_1$ | 162-46.2 | HB 187 |
| Clathrin, bovine brain | $IgG_{2a}$ | CVC.7 | TIB 138 |
| Colorectal carcinoma | $IgG_1$ | 1116-NS-19-9 | HB 8059 |
| Clq, human | IgG | 4A4B11 | HB8327 |
| Clq, human | IgG | 12A5B7 | HB 8328 |
| Diphtheria toxin | IgG (human) | 16M3F10 | HB 8363 |
| ds DNA | IgM | CH26-1352 | HB 8329 |
| DNA polymerase α | $IgG_1$ | STK 1 | CRL 1652 |
| Escherichia coli (K99 pilus) | IgG | 2BD4E4 K99 | HB 8178 |
| Fibronectin | $IgG_1$ | P3NP/PFN | HB 91 |
| Forssman antigen | IgM (rat) | M1/22.25.8.HL | TIB 121 |
| Glutamic acid decarboxylase | $IgG_1$ | GAD-1 | HB 184 |
| HLA antigens | | | |
| A2 | $IgG_{2b}$ | BB7.2 | HB 82 |
| A11 and A24 | $IgG_3$ | A11.1M | HB 164 |
| A, B, C, monomorphic | $IgG_1$ | BB7.5 | HB 120 |
| B7 and B4 | $IgG_1$ | BB7.6 | HB 115 |
| DR, DP, and DQ | $IgG_1$ | IVA12 | HB 145 |
| Ia-human, monomorphic | $IgG_{2a}$ | L243 | HB 55 |
| IgE, human | $IgG_{2a}$ | E5BB3IIA2 | HB 121 |
| IgG Fc region, human | $IgG_{2a}$ | HP 6017 | CRL 1753 |
| $IgG_{2a}$ & $IgG_{2b}$, mouse | $IgG_{2a}$ | ED1-19-1-6-5 | HB 90 |
| $IgG_{2a}$ & $IgG_{2b}$, mouse | $IgG_{2a}$ (rat) | ED1-19-1-6-5 | HB90 |
| $IgG_3$ hinge region, human | $IgG_1$ | HP 6047 | CRL 1774 |
| $IgG_4$ Fc region, human | $IgG_1$ | HP 6025 | CRL 1775 |
| IgM, Fab portion | $IgG_1$ | M-2E6 | HB 138 |
| Insulin | $IgG_1$ | CE9 H9 | HB 127 |
| Insulin, human, residue A8-10 | $IgG_1$ | AE9D6 | HB 125 |
| γ Interferon, human | $IgG_1$ | IFGCP-F1BAI0 | HB 8291 |
| Interleukin-4 | $IgG_1$ | 11B11 | HB 188 |
| Legionella pneumophila | $IgG_{2b}$ | Lpl MAB 2 | CRL 1770 |
| κ Light chains, human | $IgG_{2a}$ | HP 6053 | CRL 1758 |
| Light harvesting complex (LHC-II) | $IgG_1$ | MLH1 | CRL 1766 |
| Low density lipoprotein (LDL) receptors, rabbit | $IgG_1$ | 9D9 | CRL 1703 |
| Lung cancer, non-small cell | $IgG_{2a}{}^\kappa$ | 704A1 | HB 8302 |
| Lung cancer, small cell | IgM | SM1 | HB 8462 |
| Lymphocytes, activated, human | $IgG_1$ | OKT9 | CRL 8021 |
| Lyt 2.2 | $IgG_{2b}$ (rat) | 2.43 | TIB 210 |
| Mammary carcinoma | $IgG_1$ | B6.2 | HB 8106 |
| Melanoma | $IgG_{2a}$ | XMMME-001 | HB 8759 |
| Monoamine oxidase B, human | IgG | MAO-1C2#81 | HB 8176 |
| c-myc protein, human | $IgG_1$ | MYC CT9-B7.3 | CRL 1725 |
| v-myb protein, viral | $IgG_1$ | MYB 2-7.77 | CRL 1724 |
| Neuroblastoma cells | IgM | Mab 126 | HB 8568 |
| Null cells, human | $IgG_{2b}$ | OKM1 | CRL 8026 |
| Ornithine decarboxylase, mouse kidney | IgM | B11 | HB 8372 |
| Renin, hog | $IgG_1$ | F32 VIII C4 | CRL 1653 |
| Ricin A chain | $IgG_1$ | TFTA1 | CRL 1771 |
| Ricin B chain | $IgG_1$ | TFTB1 | CRL 1759 |
| Small cell carcinoma, human | IgM | SM1 | HB 8462 |
| T cell subset and macrophages, swine | IgMκ | 76-6-7 | HB 141 |
| T cell surface antigen, human | IgM | 2T8-3E10 | HB 8213 |
| T cells, peripheral, human | $IgG_{2a}$ | OKT3 | CRL 8001 |
| Tetanus toxoid | IgG (human) | 9F12 | HB 8177 |
| Thrombospondin | $IgG_{2a}$ | ahTSP-1 | HB 8432 |
| L-Thyroxine | $IgG_1$ | T4 clone 3 | HB 8499 |
| Transferrin receptor | $IgG_{2a}$ | L5.1 | HB 84 |
| 2, 4, 6 Trinitrophenyl | $IgG_1$ | 1B7.11 | TIB 191 |
| Viral Antigens | | | |
| Epstein-Barr virus | $IgG_1$ | 72A1 | HB 168 |
| Hepatitis B surface antigen | $IgG_1$ | H25B10 | CRL 8017 |
| Herpes simplex type 1 | $IgG_{2a}$ | 39-S | HB 8180 |
| Influenza virus | $IgG_3$ | HK-PEG-1 | CL 189 |
| Influenza A nucleoprotein | $IgG_1$ | 46/4 | HB 67 |

Those skilled in the art will realize and understand that the hybridoma cell lines listed above are merely illustrative of cell lines that can be obtained or constructed according to known methods and that such list in no way limits the present invention.

Hybridoma cells produce and secrete MAbs into the surrounding medium. Hybridomas also have MAbs of the same type and specificity associated, either integrally or passively, with the outer surface of the plasma membrane. At present, the exact mechanism by which these MAbs appear on the cell surface is unknown and in any event, the present invention does not reside in such mechanism. For the purposes of this patent, MAbs which appear on the outer cell surface and which are either integrally or passively associated with the membrane will be referred to as immunoglobulin.

The present invention utilizes the correlation between high immunoglobulin expression and high MAb secretion. This correlation is high and thus by selecting hybridomas with a high density of immunoglobulin, the general likelihood of isolating a high MAb secreting culture is greatly increased over conventional methods.

The nature of the probe used to identify and select the cells of interest may vary. The probe should accomplish two functions to enable the operation of this invention. It should first preferentially bind to the immunoglobulin located on the outer surface of the cell. Secondly, it should be able to fluoresce in a manner compatible with fluorescence activated cell sorter analysis. So long as the probe is able to accomplish these two functions, its exact composition is not critical.

Those skilled in the art will appreciate that this invention is not limited to a one step attachment of the probe to the immunoglobulin. Two part or even multipartite probes are within the scope of this invention and are within the skill of the art.

For example, biotin - avidin is a well known two part probe system. In this case, an antibody or protein which specifically binds the immunoglobulin is chemically conjugated to biotin. Such biotinylated antibodies and proteins are commercially available (see table below). Avidin, which specifically binds to biotin, is the second part of the probe and is commercially available in forms conjugated to fluorescein and Texas Red ® (Boehringer Mannheim, Indianapolis, Ind.). The biotinylated protein, which is specific for the immunoglobulin, constitutes the first part of the probe. The second part of the probe is fluorochrome labeled avidin. Thus the fluorochrome is ultimately bound to the immunoglobulin through the specificity of the biotinylated antibody or protein.

Techniques whereby a fluorescent signal is amplified, by binding antibodies to other antibodies which have already specifically bound a target, are also well known in the field of immunology and are considered multipartite probes. An example of such a probe is constructed from goat antiserum, that is specific for mouse immunoglobulins, and is bound by sheep antiserum that is specific for goat antibodies. Then, fluorochrome tagged rabbit antibodies, that specifically bind sheep antibodies, are allowed to bind to the sheep antibodies. In this instance, the goat antiserum is the part of the probe which specifically binds the immunoglobulin located on the surface of a mouse hybridoma. The fluorochrome labeled rabbit serum is the part of the probe which fluoresces. The goat and sheep antiserum are the components of the probe which link the fluorescent portion to the probe part which specifically binds to the cell surface immunoglobulin.

A generalized probe which binds to the Fc region of any antibody produced by a given species may also be used. These types of probes are standard immunological reagents which include MAbs and antisera raised against various types of antibody classes in different host species. MAbs and antisera are purified and immunoabsorbed to insure proper specificity. The purified reagant is then chemically coupled to a standard fluorochrome such as fluorescein, rhodamine, Texas Red ®, phycoerythrin or phycocyanin. Many commercial sources for this probe type exist. Some examples follow:

| Source | Specificity | Fluorochrome | Company |
| --- | --- | --- | --- |
| Rat (MAb) | Mouse Kappa Chain | Fluorescein | Amac Inc.: Westbrook, ME |
| Mouse (MAb) | Rabbit IgG | (Biotin) | Amac Inc: Westbrook, ME |
| Rabbit | Human IgG | Rhodamine | Calbiochem: San Diego, CA |
| Goat | Human IgG | Rodamine | Calbiochem: San Diego, CA |
| Goat | Mouse IgG | Rhodamine | Calbiochem: San Diego, CA |
| Goat | Mouse IgM | Rhodamine | Calbiochem: San Diego, CA |
| Goat | Rabbit IgG | Rhodamine | Calbiochem: San Diego, CA |
| Goat | Rat IgG | Rhodamine | Calbiochem: San Diego, CA |
| Goat | Mouse IgG | Texas Red ® | Calbiochem: San Diego, CA |
| Goat | Rat IgG | Texas Red ® | Calbiochem: San Diego, CA |
| Goat | Rabbit IgG | Phycoerythrin | Calbiochem: San Diego, CA |
| Goat | Human IgG | Phycoerythrin | Calbiochem: San Diego, CA |
| Goat | Mouse IgG | Phycocyanin | Calbiochem: San Diego, CA |
| Goat | Mouse IgA | (Biotin) | Calbiochem: San Diego, CA |
| Sheep | Human IgG-Fc | Fluorescein | Cappel: Malvern, PA |
| Goat | Mouse IgG | Rhodamine | Cappel: Malvern, PA |
| Rabbit | Human IgG | Texas Red ® | Cappel: Malvern, PA |
| Goat F(ab')$_2$ | Mouse IgG | Fluorescein | Cappel: Malvern, PA |
| Goat | Human IgE | Fluorescein | Cappel: Malvern, PA |
| Rabbit | Human IgG | Fluorescein | Cappel: Malvern, PA |
| Sheep | Human IgG | Fluorescein | Cappel: Malvern, PA |
| Rat (MAb) | Rabbit IgG | Rhodamine | Jansen, Inc.: Piscataway, NY |
| Mouse (MAb) | Rat IgD | Rhodamine | Jansen, Inc: Piscataway, NY |
| Rat (MAb) | Mouse IgG$_2$⊕ | Fluorescein | Pandex Division: Mundelein, IL |
| Rat (MAb) | Mouse IgM | Fluorescein | Pandex Division: Mundelein, IL |
| Mouse (MAb) | Mouse Kappa Chain | Fluorescein | Pandex Division: Mundelein, IL |
| Rat (MAb) | Rabbit IgG | Fluorescein | Sera Lab: Westbury, NY |
| Mouse (MAb) | Rat IgG$_{2b}$ | Fluorescein | Sera Lab: Westbury, NY |
| Mouse (MAb) | Rat IgG$_{2a}$ | Fluorescein | Sera Lab: Westbury, NY |
| Rat (MAb) | Mouse IgG$_1$ | Fluorescein | Zymed: San Fran. CA |
| Mouse (MAB) | Human IgG$_1$ | (Biotin) | Zymed: San Fran. CA |
| Mouse (MAb) | Human IgG$_{2a}$ | (Biotin) | Zymed: San Fran. CA |
| Rat (MAb) | Mouse IgG$_{2a}$ | (Biotin) | Zymed: San Fran. CA |
| Rat (MAb) | Mouse IgG$_{2b}$ | (Biotin) | Zymed: San Fran. CA |
| Rat (MAb) | Mouse IgM | (Biotin) | Zymed: San Fran. CA |
| Goat | Human IgG | (Biotin) | Zymed: San Fran. CA |

Those skilled in the art will realize and understand that the probes listed above are merely illustrative of probes that can be obtained or constructed according to known methods and that such list in no way limits the present invention.

The particular antigen to which the Fab region of the immunoglobulin binds can also be used as a probe providing the antigen has been tagged with a fluorochrome or has inherent fluorescent properties. For example, if a hybridoma culture producing MAbs specific for insulin were to be selectively cloned using this invention, fluorescein labeled insulin (Sigma Chemical Co., St. Louis, Mo.) could be used as the specific probe. Two other examples of antigen type probes are fluorescein labeled bovine serum albumin and fluorescein labeled dog serum albumin, both of which are commercially available (Sigma Chemical Co., St. Louis, Mo.). These reagents could be used as probes when using the invention on hybridoma cultures that produce MAbs specific for bovine serum albumin and dog serum albumin respectively.

Since virtually all purified proteins can be readily fluoresceinated using well established techniques, antigen type probes can be constructed which are suitable for use with the invention. Commercially available, purified, illustrative proteins such as carcinoembryonic antigen (CEA: Biodesign Inc., Kennebunkport, Me.), human chorionic gonadotropin (hCG: Cambridge Medical Diagnostics Inc., Billerica, Mass.), and human growth hormone (hGH: Hybritech, San Diego, Calif.) can be fluorochrome labeled. Once tagged with a fluorochrome, these proteins are suitable probes when utilizing the invention on hybridoma cultures which produce MAbs directed against CEA, hCG and hGH respectively. Using established techniques for labeling proteins, a great variety of antigen probes can be constructed which are useful in the invention.

A hapten is a chemical compound which is unable to elicit an immunological response on its own. However, when the compound is conjugated to a true immunogen, the immune system is able to respond and form antibodies to the previously non-immunogenic compound. One such immunogen is the keyhole lympet hemocyanin (KLH) protein. The antibiotic actinomycin-D (Act-D: Sigma Chemical Co.; St. Louis, Mo.) is an example of a haptenic substance. When the immune system is challenged with Act-D it is unable to respond. Once coupled to KLH, Act-D acts as an antigenic epitope on the highly immunogenic KLH protein. Hybridomas which secrete MAbs directed towards Act-D have been constructed. Skilled artisans will understand that a fluorochrome can be coupled directly to Act-D or to a carrier protein such as KLH by conventional means and that the resultant conjugate can be used as a probe in this invention. Other hapten probes can be constructed in a similar fashion. Haptenic compounds such as 2,4-dinitrophenol and 2,4,6-trinitrophenol when coupled to fluorochrome labeled carrier molecules such as KLH are suitable hapten probes for the invention.

Many other possibilities exist for constructing hapten probes. Compounds such as phosphocholine and phosphotyrosine (Boehringer Mannheim, Indianapolis, Ind.) have been used as haptens to generate MAbs. These compounds are suitable hapten probes for the invention when conjugated to a fluorochrome labeled carrier protein. In general, any compound capable of eliciting an immune response as a hapten can either be directly labeled with a fluorochrome or be conjugated to a fluorochrome labeled carrier protein and used as a hapten probe in the invention.

A particular antigen or hapten could possess the appropriate fluorescent characteristics to enable the use of the native antigen or hapten itself as the probe in the invention. Examples of this specialized situation would include all of the standard fluorochromes fluorescein, rhodamine, Texas Red ®, phycoerythrin and phycocyanin when used as haptens.

The descriptions used to illustrate the invention use a fluorescence activated cell sorter (for a brief overview see Herzenberg et al., 1976, Fluorescence activated cell sorting. *Sci. Amer.* 234, 108; for an in depth analysis see *Flow Cytometry and Sorting*, eds. Melamad, Mullaney and Mendelsohn. John Wiley and Sons, Inc., New York, 1979). Briefly, fluorescence activated cell sorters take a suspension of cells and pass them single file by a laser placed near a detector. The detector measures the fluorescent intensity of each cell as it passes through the instrument and generates a histogram plot of cell number versus fluorescent intensity. Gates or limits can be placed on the histogram thus identifying a particular population of cells. The instrument is then instructed to electrostatically separate the selected cells away from all the other cells. In the batch mode, the fluorescence activated cell sorter will deflect those cells which fall within the gated area into a common vessel. The resultant batch collected culture is not a monoclonally derived culture and is, therefore, genetically heterogeneous at the time the selection process is completed. The heterogeneous condition does not negate the fact that the newly batch sorted culture will secrete MAb at a higher rate than did the culture from which it was derived.

Currently, fluorescence activated cell sorters can be equipped with automated cell cloning devices. Such a device enables one to instruct the instrument to singly deposit a selected cell into an individual growth well. The preferred method of operating the invention is to establish a new culture by depositing a selected single cell into a growth well where it is allowed to grow into a monoclonally derived hybridoma culture. Thus, genetic homogeneity is established within the newly cloned culture.

In an isolation according to the present invention, the cell sorter is set up to select those cells having the highest probe intensity, usually a small fraction of the cells in the culture. The level of intensity at which the sorter is set and the fraction of cells which is selected, depend on the condition of the parent culture and the objective of the isolation. In general, the operator should first sort an aliquot of the culture, and record the histogram of intensity versus number of cells. The operator can then set the selection level and isolate an appropriate number of the most active cells.

The invention is particularly useful when a culture's MAb secreting capacity has deteriorated to such a point that MAb is no longer detectable in the spent medium. The cell line is now considered an essentially non-secreting culture. This phenomenon is well known to those skilled in the art and occurs relatively often for reasons discussed in the Background section. Even though MAb levels are below the detection limits of several very sensitive assays, the culture is not totally non-secreting. In an essentially non-secreting culture, cells which retain the ability to secrete MAb may be in the range of one in 1,000 to one in 10,000. A viable, secreting culture can be isolated from an essentially non-secreting culture using conventional cloning techniques but only through very aggressive, extensive and time consuming efforts. The invention circumvents the laborious and time consuming process of randomly cloning cells which have already lost their capacity to secrete MAb. The invention enables one to sort through hundreds of thousands of cells in a matter of minutes and identify and capture those vanishingly few cells which are still able to secrete MAb.

Regardless of the cloning technique used, the resultant hybridoma cultures must be screened for MAb production and specificity. A wide variety of techniques and methods for measuring these parameters is described in the scientific literature.

It should be stressed that the present invention is not limited to conventional hybridoma cells. Methods utilizing any cell type that produces and secretes a MAb of known specificity are within the scope of the present invention. The invention is not limited by the type of MAb produced. Methods utilizing cells which produce chimeric antibodies, MAbs of any species, bifunctional MAbs and multispecific MAbs are all within the scope of the present invention.

EXAMPLE 1

L2-KS

The murine hybridoma cell line L2-KS has been described in detail (Starling et al., 1989, In vivo efficacy of monoclonal antibody-drug conjugates of three different subisotypes which bind the human tumor-associated antigen defined by the KS $\frac{1}{4}$ antibody. C.I.I. 28, 171) and is available through the American Type Culture Collection under HB 9940. Briefly, it is a murine hybridoma which secretes an $IgG_1$ MAb that reacts with a 40,000 dalton human tumor associated glycoprotein known as KS $\frac{1}{4}$ (Varki et al., 1984, Antigens associated with a human lung adenocarcinoma defined by monoclonal antibodies. Cancer Res. 44, 681.)

All flow cytometric cell sorting was done with an Epics C (Coulter Epics Division, Hialeah, Fla.) flow cytometer-cell sorter (FCCS). Hybridoma cells were excited with 600 MW of 488 nm light emitted from an argon ion laser. The resultant cell-associated fluorescence light was captured through 488 interference and 515 long pass absorbance optical filters. The optical alignment of the FCCS instrument was optimized and the fluorescence readings obtained were standardized using uniform fluorospheres. The flow cytometer was outfitted with an automated cloning accessory called an "AUTO-CLONE®" (Coulter Epics Division, Hialeah, Fla.) which can be instructively programmed to dispense a single particle or cell into selected compartment of a standard 96 well microtiter culture plate. The sort delay timing was assured by microscopic observation of sorted fluorospheres. In a test evaluation of the AUTO-CLONE®, a single fluorosphere was programmed to be deposited into wells of three separate microtiter plates. Upon fluorescence microscopic inspection, each of the 288 wells had exactly 1 fluorosphere, with no doublets and no misses. The cell-contact components of the FCCS were sterilized prior to cloning by flushing with 95% ethanol for 30 min followed by exhaustive rinsing in sterile phosphate buffer saline (PBS; GIBCO; Grand Island, N.Y.) sheath fluid.

Cells were prepared for sorting by harvesting $1-3 \times 10^6$ hybridoma cells and incubating them in 1 ml of a 1:10 dilution of F(ab')$_2$ fragments of goat-anti-mouse-IgG-FITC (AMIGG-FITC; Cappel, Cat #1311-0081, West Chester, Pa.) for 45 min on ice followed by two washes in culture medium (HL-1; Ventrex Labs; Portland, Mass.: supplemented with 10% fetal bovine serum; Hyclone; Ogden, Utah). 200 $\mu$l of a 50 $\mu$g/ml solution of propidium iodide (PI, Sigma Chemical Co., St. Louis, Mo.) was added to 1 ml of the cell preparation just prior to sorting to help define and select viable cells.

Subpopulations of cells to be sorted were FCCS defined by either rectilinear gates or by polygonal bitmaps of collected two parameter (FALS vs. log green fluorescence) histograms. A three droplet sorting procedure was employed to help assure maximum purity (per manufacturer's instructions). Single hybridoma cells were deposited into microtiter wells which were seeded 24 hr. previously with $5 \times 10^6$ C3H/HeJ thymocyte feeder cells (Jackson Labs; Bar Harbor, Mass.) in 200 $\mu$L of culture medium.

MAb concentrations in the spent culture media were determined by automated laser nephelometry using a Behring Laser Nephelometer (Behring Diagnostics, La Jolla, Calif.). Concentrations are expressed ug/ml/72 hours and have been normalized to one million cells. Results appear in Table 1 which further exemplify the present invention.

EXAMPLE 2

L1-KS

The murine hybridoma cell line L1-KS has been described in detail (Starling et al. supra). It secretes an $IgG_{2b}$ MAb that reacts with the KS $\frac{1}{4}$ antigen. Cloning was performed in substantial accordance with the teachings of Example 1. Results appear in Table 1 which further exemplify the present invention.

EXAMPLE 3

L4-KS

The murine hybridoma cell line L4-KS has been described in detail (Starling et al. supra). It secretes an $IgG_{2a}$ MAb that reacts with the KS $\frac{1}{4}$ antigen. Cloning was performed in substantial accordance with the teachings of Example 1. Results appear in Table 1 which further exemplify the present invention.

EXAMPLE 4

14-95-55

The murine hybridoma cell line 14-95-55 produces an $IgG_{2a}$ MAb that reacts with CEA. This line was an essentially non-secreting culture at the time it was used in the invention. Cloning was performed in substantial accordance with the teachings of Example 1. Results appear in Table 1 which further exemplify the present invention.

TABLE 1

| Hybridoma Name | Secretion Rate Pre-invention ug/ml/72 hrs/ 1 × 10$^6$ cells | Secretion Rate Post-invention ug/ml/72 hrs/1 × 10$^6$ cells |
| --- | --- | --- |
| L1-KS | 10.9 | 34.1 |
| L2-KS | 8.2 | 18.5 |
| L4-KS | 6.8 | 25.1 |
| 14-95-55 | <1.5 | 40.8 |

We claim:

1. A method of selectively isolating a population of hybridoma cells which secrete monoclonal antibody (Mab) of known specificity at a level higher than a parent culture from which the population was selectively isolated comprising:

a) contacting, in a liquid medium, an immunoglobulin associated with, and presented on the outer surface of the population of cells, which secrete Mab of known specificity, with a probe capable of preferentially binding immunoglobulin present on the population of cells; and b) isolating those cells with high probe intensity by means of a cell sorter.

2. The method of claim 1 wherein the culture is a hybridoma culture, the probe is fluorescent and the cell sorter is a fluorescence activated cell sorter.

3. The method of claim 2 wherein the probe is a fluorochrome-tagged antiserum.

4. The method of claim 2 wherein the probe is a fluorochrome-tagged monoclonal antibody.

5. The method of claim 2 wherein the probe is a fluorochrome-tagged antigenic substance.

6. The method of claim 2 wherein the probe is a fluorochrome-tagged haptenic substance.

7. The method of claim 1 wherein the selected population of cells are individually deposited into separate growth wells by means of a cell sorter outfitted with an automated cloning accessory.

8. The method of claim 7 wherein the culture is a hybridoma culture, the probe is fluorescent and the cell sorter is a fluorescence activated cell sorter.

9. The method of claim 8 wherein the probe is a fluorochrome-tagged antiserum.

10. The method of claim 8 wherein the probe is a fluorochrome-tagged monoclonal antibody.

11. The method of claim 8 wherein the probe is a fluorochrome-tagged antigenic substance.

12. The method of claim 8 wherein the probe is a fluorochrome-tagged haptenic substance.

13. A method of claim 2 wherein the parent culture is essentially non-secreting.

14. A method of claim 3 wherein the parent culture is essentially non-secreting.

15. A method of claim 4 wherein the parent culture is essentially non-secreting.

16. A method of claim 5 wherein the parent culture is essentially non-secreting.

17. A method of claim 6 wherein the parent culture is essentially non-secreting.

18. A method of claim 7 wherein the parent culture is essentially non-secreting.

19. A method of claim 8 wherein the parent culture is essentially non-secreting.

20. A method of claim 9 wherein the parent culture is essentially non-secreting.

21. A method of claim 10 wherein the parent culture is essentially non-secreting.

22. A method of claim 11 wherein the parent culture is essentially non-secreting.

23. A method of claim 12 wherein the parent culture is essentially non-secreting.

24. A method of claim 1 wherein the parent culture is essentially non-secreting.

* * * * *